US00PP20545P2

(12) United States Plant Patent
Bergman

(10) Patent No.: US PP20,545 P2
(45) Date of Patent: Dec. 8, 2009

(54) ***CHRYSANTHEMUM* PLANT NAMED 'YOESSEX'**

(50) Latin Name: *Chrysanthemum×morifolium*
Varietal Denomination: Yoessex

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/283,271

(22) Filed: Sep. 8, 2008

(51) Int. Cl.
*A01H 5/00* (2006.01)

(52) U.S. Cl. ..... Plt./286

(58) Field of Classification Search ..... Plt./286
See application file for complete search history.

(56) References Cited

U.S. PATENT DOCUMENTS

PP11,203 P * 2/2000 VandenBerg

OTHER PUBLICATIONS

Plant Varieties Journal Jul. 2008 No. 68 112 pages See especially p. 13.*

* cited by examiner

*Primary Examiner*—Wendy C Haas
(74) *Attorney, Agent, or Firm*—C. A. Whealy

(57) ABSTRACT

A new and distinct cultivar of *Chrysanthemum* plant named 'Yoessex', characterized by its upright, outwardly spreading and uniformly mounded plant habit; moderately vigorous growth habit; freely branching habit; dark green-colored foliage; uniform, freely and early flowering habit; daisy-type inflorescences with purple-colored ray florets and green-colored disc florets; and excellent postproduction longevity.

1 Drawing Sheet

Botanical designation: *Chrysanthemum×morifolium.*
Cultivar denomination: 'Yoessex'.

BACKGROUND OF THE INVENTION

The present invention relates to a new and distinct cultivar of *Chrysanthemum* plant, botanically known as *Chrysanthemum×morifolium*, commercially grown as a pot-type *Chrysanthemum* and hereinafter referred to by the name 'Yoessex'.

The new *Chrysanthemum* is a product of a breeding program conducted by the Inventor in Fort Myers, Fla. The objective of the breeding program is to create new pot-type *Chrysanthemum* cultivars that are suitable for year-round production with uniform plant growth habit, freely branching habit, good vigor, desirable inflorescence form and floret colors, fast response time and excellent postproduction longevity.

The new *Chrysanthemum* originated from a cross-pollination made by the Inventor in February 2003, in Salinas, Calif. of a proprietary selection of *Chrysanthemum×morifolium* identified as code number YB-A2654, not patented, as the female, or seed, parent with a proprietary selection of *Chrysanthemum×morifolium* identified as code number YB-A2409, not patented, as the male, or pollen, parent. The new *Chrysanthemum* was discovered and selected by the Inventor as a single flowering plant within the progeny of the stated cross-pollination in a controlled greenhouse environment in Fort Myers, Fla. in November, 2003.

Asexual reproduction of the new *Chrysanthemum* by vegetative tip cuttings was first conducted in a controlled greenhouse environment in Fort Myers, Fla. in February 2004. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoessex'. These characteristics in combination distinguish 'Yoessex' as a new and distinct pot-type *Chrysanthemum* cultivar:

1. Compact, upright, outwardly spreading and uniformly mounded plant habit.
2. Moderately vigorous growth habit.
3. Freely branching habit.
4. Dark green-colored foliage.
5. Uniform, freely and early flowering habit.
6. Daisy-type inflorescences with purple-colored ray florets and green-colored disc florets.
7. Excellent postproduction longevity with inflorescences maintaining good substance and color for about four to five weeks in an interior environment.

Plants of the new *Chrysanthemum* differ from plants of the female parent selection primarily in ray floret color as plants of the female parent selection have pink-colored ray florets.

Plants of the new *Chrysanthemum* differ from plants of the male parent selection primarily in ray floret color as plants of the male parent selection have dark pink-colored ray florets. In addition, plants of the new *Chrysanthemum* do not produce pollen whereas plants of the male parent selection produce pollen.

Plants of the new *Chrysanthemum* can be compared to plants of *Chrysanthemum×morifolium* 'Yolompoc', disclosed in U.S. Plant Pat. No. 11,203. In side-by-side comparisons conducted in Fort Myers, Fla., plants of the new *Chrysanthemum* primarily from plants of 'Yolompoc' in the following characteristics:

1. Plants of the new *Chrysanthemum* had larger inflorescences than plants of 'Yolompoc'.
2. Plants of the new *Chrysanthemum* and 'Yolompoc' differed in ray floret color as plants of 'Yolompoc' had red purple-colored ray florets.

BRIEF DESCRIPTION OF THE PHOTOGRAPHS

The accompanying photographs illustrate the overall appearance of the new *Chrysanthemum*. These photographs shows the colors as true as it is reasonably possible to obtain in colored reproductions of this type. Colors in the photographs may differ slightly from the color values cited in the detailed botanical description which accurately describe the colors of the new *Chrysanthemum*. The photograph at the bottom of the sheet 'Yoessex' grown in a container. The photograph at the top of the sheet is a close-up view of typical inflorescences of 'Yoessex'.

DETAILED BOTANICAL DESCRIPTION

The aforementioned photographs and following observations and measurements describe plants grown in Leamington, Ontario, Canada during the late spring in a glass-covered greenhouse and under conditions and practices which approximate those generally used in commercial pot-type *Chrysanthemum* production. During the production of the plants, day temperatures ranged from 20° C. to 24° C., night temperatures ranged from 15° C. to 17° C. and light levels ranged from 4,000 to 6,000 foot candles. Four unrooted cuttings were directly stuck in 15-containers, exposed to long day/short night conditions, and pinched about two weeks later. One week after the pinch, the photoinductive short day/long night treatments were started. Plants used in the photographs and for the description had been growing for ten weeks and were grown as spray-types. In the following description, color references are made to The Royal Horticultural Society Colour Chart, 2001 Edition, except where general terms of ordinary dictionary significance are used.

Botanical classification: *Chrysanthemum×morifolium* 'Yoessex'.

Parentage:

*Female, or seed, parent.*—Proprietary selection of *Chrysanthemum×morifolium* identified as code number YB-A2654, not patented.

*Male, or pollen, parent.*—Proprietary selection of *Chrysanthemum×morifolium* identified as code number YB-A2409, not patented.

Propagation:

*Type.*—Terminal vegetative cuttings.

*Time to initiate roots.*—About four days at temperatures of 21° C.

*Time to produce a rooted young plant.*—About ten days at temperatures of 21° C.

*Root description.*—Fine to thick, fibrous; white in color.

*Rooting habit.*—Freely branching; moderately dense.

Plant description:

*Appearance.*—Herbaceous daisy pot-type *Chrysanthemum* typically grown as a natural spray type. Compact; stems upright and outwardly spreading giving a uniformly mounded appearance to the plant. Freely branching habit, about five to six lateral branches develop after removal of terminal apex (pinching); dense and full plant habit. Moderately vigorous growth habit.

*Plant height.*—About 22.5 cm.

*Plant width.*—About 21.5 cm.

*Lateral branches.*—Length: About 20 cm. Diameter: About 4 mm. Internode length: About 2.4 cm. Strength: Strong. Texture: Pubescent; longitudinally ridged. Color: Close to 146A.

Foliage description:

*Arrangement.*—Alternate, simple.

*Length.*—About 6 cm.

*Width.*—About 4.4 cm.

*Shape.*—Palmately lobed.

*Apex.*—Cuspidate.

*Base.*—Attenuate.

*Margin.*—Palmately lobed, sinuses between lateral lobes parallel.

*Texture, upper and lower surfaces.*—Fine pubescence; veins prominent on lower surface.

*Color.*—Developing leaves, upper surface: Close to 147A. Developing leaves, lower surface: Close to 137B. Fully expanded leaves, upper surface: Close to N137B; venation, close to 147B. Fully expanded leaves, lower surface: Close to 137B; venation, close to 147B.

*Petiole.*—Length: About 1.8 cm. Diameter: About 3.5 mm. Texture, upper and lower surfaces: Pubescent. Color, upper and lower surfaces: Close to 147B.

Inflorescence description:

*Appearance.*—Daisy-type inflorescence form with elongated oblong-shaped ray florets. Inflorescences borne on terminals above foliage. Disc and ray florets arranged acropetally on a capitulum. Typically grown as a spray-type.

*Fragrance.*—Faint; slightly sour.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to two weeks of long day/short night conditions followed by photoinductive short day/long night conditions flower about 7.5 weeks later.

*Postproduction longevity.*—Inflorescences maintain good color and substance for about four to five weeks in an interior environment; inflorescences persistent.

*Quantity of inflorescences.*—Freely flowering, about five to six inflorescences develop per lateral stem.

*Inflorescence bud.*—Height: About 2 cm. Diameter: About 1.3 cm. Shape: Ovoid. Color: Close to N77B.

Inflorescence size.—Diameter: About 7 cm. Depth (height): About 2.8 cm. Diameter of disc: About 1.8 cm. Receptacle height: About 8 mm. Receptacle diameter: About 1.7 cm. Receptacle color: Close to N137C.

*Ray florets.*—Shape: Elongated oblong. Orientation: Initially upright, with development, close to 55° from vertical. Aspect: Mostly flat; apices reflexing. Length: About 4.2 cm. Width: About 1 cm. Apex: Emarginate. Base: Attenuate; short corolla tube. Margin: Entire. Texture, upper and lower surfaces: Smooth, glabrous; velvety. Number of ray florets per inflorescence: About 24 arranged in about two whorls.

*Color.*—When opening, upper surface: Close to 71A. When opening, lower surface: Close to N78C. Fully opened, upper surface: Close to N79C; color does not fade with development. Fully opened, lower surface: Close to N78C; color does not fade with development.

*Disc florets.*—Arrangement: Massed at center of receptacle. Shape: Tubular, elongated. Apex: Five-pointed. Length: About 8 mm. Diameter: About 2 mm. Number of disc florets per inflorescence: About 252. Color, immature: Apex: Close to 154B. Mid-section: Close to 145C. Base: Close to 145D. Color, mature: Apex: Close to 154A. Mid-section: Close to 154C. Base: Close to 145D.

*Phyllaries.*—Number of phyllaries per inflorescence: About 20 arranged in about two whorls. Length: About 1 cm. Width: About 3 mm. Shape: Narrowly elliptical. Apex: Acute. Base: Truncate. Margin: Entire. Texture, upper surface: Smooth, glabrous; waxy. Texture, lower surface: Pubescent. Color, upper surface: Close to 146A. Color, lower surface: Close to 147B.

*Peduncles.*—Length: About 6.3 cm. Diameter: About 2 mm. Angle: About 45° from vertical. Strength: Strong, flexible. Texture: Pubescent. Color: Close to 147B.

*Reproductive organs.*—Androecium: Present on disc florets only. Filament length: About 1 mm. Filament color: Close to 157D. Anther shape: Oblong. Anther length: About 1 mm. Anther color: Close to 9A. Pollen amount: None observed. Gynoecium: Present on both ray and disc florets. Pistil length: About 9 mm. Stigma shape: Bi-parted. Stigma color: Close to 7A. Style length: About 7 mm. Style color: Close to 145C. Ovary color: Close to 157D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* tolerate temperatures ranging from about 5° C. to about 38° C.

It is claimed:

1. A new and distinct *Chrysanthemum* plant named 'Yoessex,' as illustrated and described.

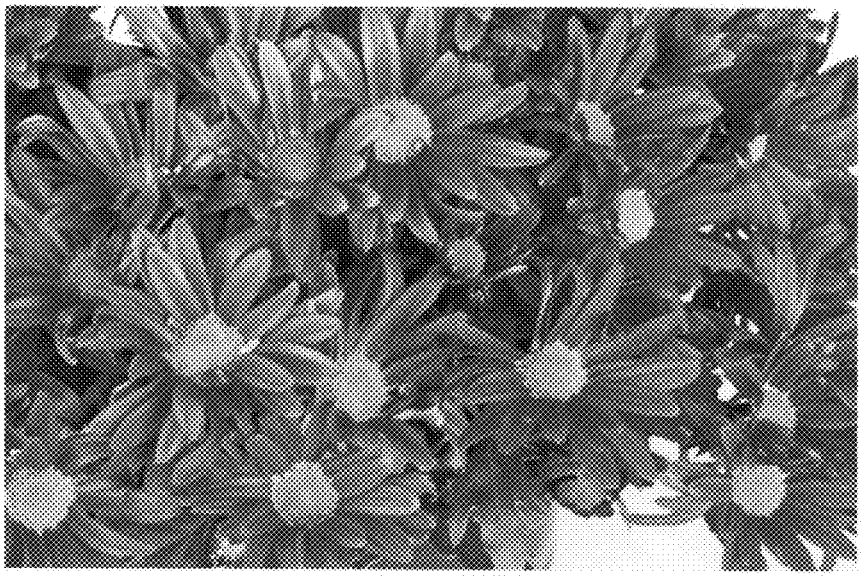
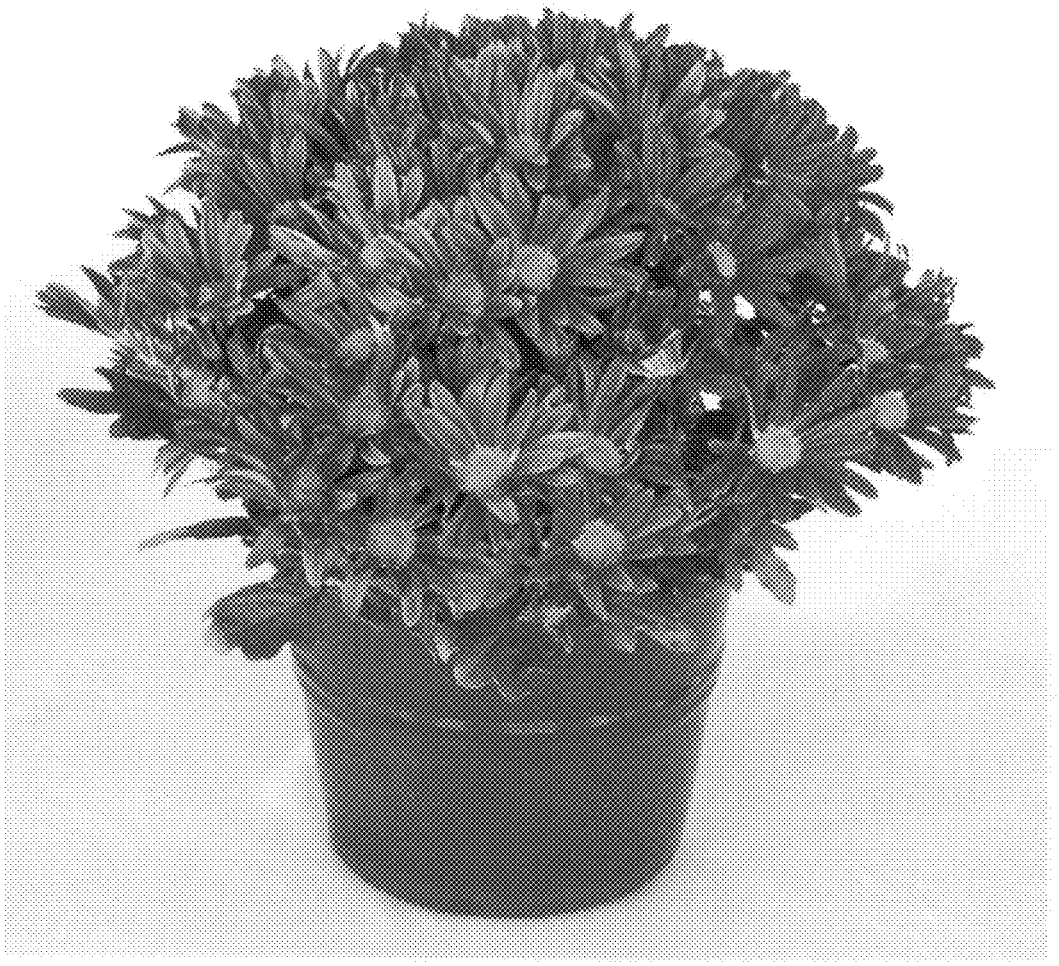

* * * * *